(12) United States Patent
Chen

(10) Patent No.: US 7,897,105 B2
(45) Date of Patent: Mar. 1, 2011

(54) PH INDICATOR

(76) Inventor: Itay Shlomo Chen, Haifa (IL)

( * ) Notice: Subject to any disclaimer, the term of this patent is extended or adjusted under 35 U.S.C. 154(b) by 875 days.

(21) Appl. No.: 11/748,295

(22) Filed: May 14, 2007

(65) Prior Publication Data

US 2008/0286148 A1    Nov. 20, 2008

(51) Int. Cl.
  *G01N 31/00* (2006.01)
  *G01N 31/22* (2006.01)
(52) U.S. Cl. ............ 422/55; 422/61; 422/68.1; 436/163; 436/164
(58) Field of Classification Search .................... 422/55, 422/61, 68.1; 436/163–164
See application file for complete search history.

(56) References Cited

U.S. PATENT DOCUMENTS 6,395,551 B1 *   5/2002   Kipke et al. ...................... 436/1
6,801,477 B2 *  10/2004   Braunberger ................ 368/327

* cited by examiner

*Primary Examiner* — Lyle A Alexander
(74) *Attorney, Agent, or Firm* — Hogan Lovells US LLP

(57) ABSTRACT

A pH indicator comprising a solid substrate coated at least partially by at least one layer of at least one substance, wherein said the and the substrate are having different colors and wherein the at least one substance is selected to dissolve or to decompose when exposed to predetermined pH values, thereby exposing said first color.

14 Claims, 2 Drawing Sheets

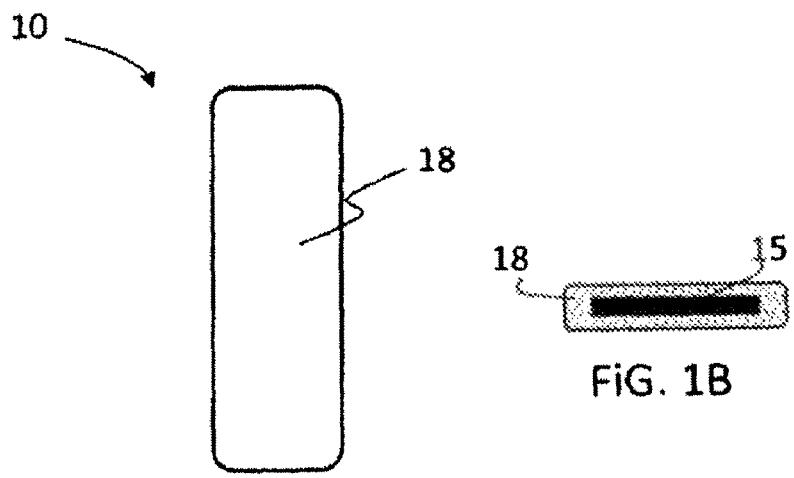
FIG. 1A
FIG. 1B
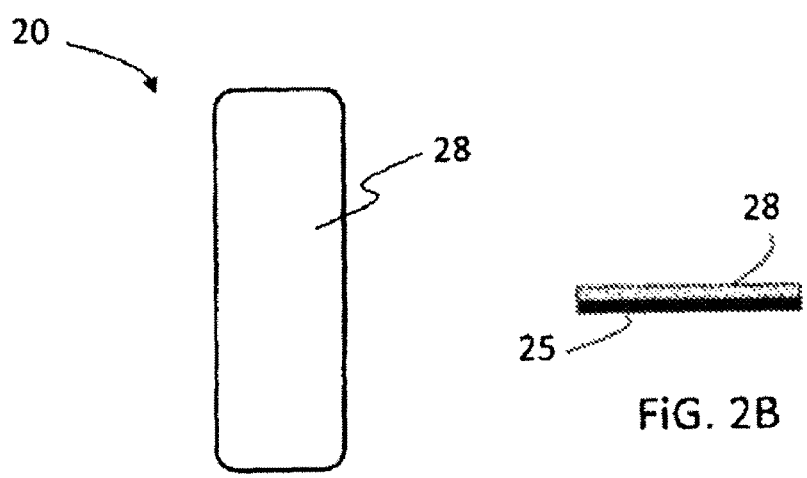
FIG. 2A
FIG. 2B
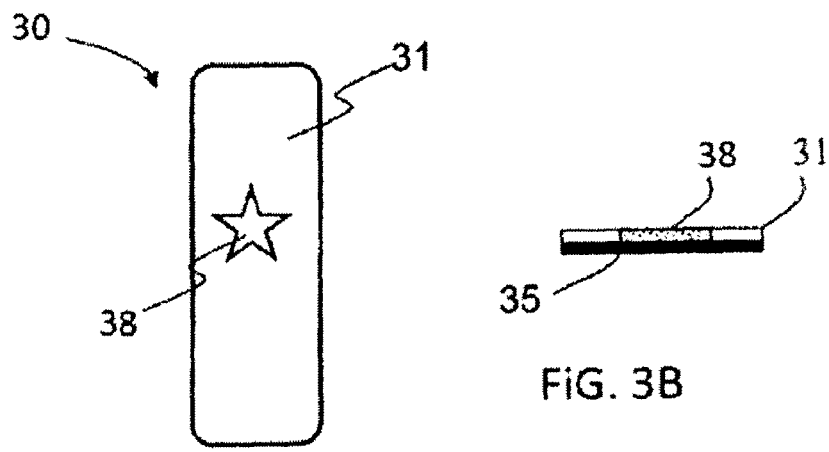
FIG. 3A
FIG. 3B

PH INDICATOR

BACKGROUND OF THE INVENTION

1. Field of the Invention

The present invention generally relates to pH indicators and more specifically to a novel type of pH indicator sticks coated by substances having pH-depending solubility properties, for the detection of pH transitions.

2. Discussion of the Related Art

There are many cases where a change in the pH level below or above a certain value reflects a crucial change of a condition or a crucial stage during a process. For example, pH of bodily fluids and secretions are used for diagnosing various biological conditions. A deviation from the normal value may indicate abnormal condition. For example, studies have shown that pH of vaginal fluid which is equal to or greater than 4.6 may be a symptom of bacterial vaginosis or candida. Another example is food products where the drop of the pH level may indicate spoilage of food. Although it is now mandatory in most countries to indicate an expiration date on food products, the indicated expiration date is estimation only and does not necessarily reflect the real status of the particular food product. Many more other examples are known in various industrial applications.

Accurate measurements of pH are conducted potentiometrically by using a pH-meter with pH-selective electrode. However, such measurements are not always feasible or worthwhile. Moreover, many times it is sufficient to only know whether the pH falls below and/or elevates above a specific threshold value while it is of less importance to know the exact pH value before the transition occurs. For this reason it is a common practice to use pH indicators which have different color at different pH values. pH indicators having pH dependent color are well known for many years. They consist of compounds, usually weak bases or acids that, due to differences in electronic configuration, have a different visible color in their neutral and charged forms. Small amounts of such pH indicator compounds can be added directly to test samples or alternatively, the compounds are impregnated onto a substrate, typically paper strips, to form pH indicator strips. However, the reading and interpretation of such pH indicators is subjective. Interpretation is particularly ambiguous at the pH range where the indicator turns its color (pKa) i.e., where both forms of the compound are present. Moreover, indicator strips tend to lose their pH indicative color upon drying, therefore reading has to be made immediately which is not always possible.

The present invention provides a new type of pH indicators which is based on pH dependent solubility properties. The indicators of the invention give a clear visible signal (a color signal) when a predetermined pH change occurs. The invention provides a full spectrum of indicators which can be designed for a specific pH transition and specific use. By selecting the appropriate substances, the novel indicators may be adjusted to accurately detecting any desirable pH change. For example, suitable substances may be selected to provide a pH indicator that changes color only in the range 4<pH<6 but maintains its default color in all other pH values. Another type of indicators may be prepared that give a signal when the pH changes above or below one or more predetermined thresholds. For example, by selecting the appropriate substances, an indicator may be designed to react only when pH>10 or pH<3 but remains unchanged when 3<pH<10. Moreover, the novel indicators may be tailored to indicate a particular pH change in an expected non-monotonic pH behavior. For example if during a process the pH is known to first elevate and then to fall again so as to pass through the same pH value twice but it is only the second time that should be indicated.

The pH indicators of the invention may be stand alone indicators configured as sticks or strips to be immersed into a test sample, or may be incorporated into a variety of articles including, but not limited to, food products and disposable absorbent articles such as hygienic pads and panty shields.

SUMMARY OF THE PRESENT INVENTION

It is a general object of the present invention to provide a novel type of pH indicators which give a clear visible signal upon a pH transition below or above a predetermined threshold or a predetermined range.

A further object of the invention is to provide such an indicator which can be designed for a specific pH transition and a specific use.

Yet a further object of the invention to provide a pH indicator which is based on pH-depending solubility properties.

Other objects and advantages of the invention will become apparent from the following description.

In accordance with the above objects there is provided a pH indicator comprising a solid substrate coated at least partially by at least one layer of at least one substance wherein the at least one layer is having a first color and wherein the substrate is having a second color different from the first color. The at least one substance is selected to dissolve or to decompose when exposed to predetermined pH values, thereby exposing said second color. The at least one coating layer may be applied to both faces of the substrate or to only one face and may cover the whole face or be applied in a discontinuous manner to form a predetermined pattern.

In accordance with one embodiment of the invention, the at least one coating layer is essentially insoluble at pH values lower than a preselected pH value and essentially soluble at pH values higher than said preselected pH value.

In accordance with another embodiment, the at least one coating layer is essentially insoluble at pH values higher than a preselected pH value and essentially soluble at pH values lower than said preselected pH value.

In accordance with yet another embodiment the at least one coating layer is essentially insoluble in a pH range delimited by a lower pH limit and an upper pH limit and essentially soluble at pH values lower than said lower pH limit or higher than said upper pH limit.

Yet in accordance with a further embodiment the at least one coating layer is essentially soluble in a pH range delimited by a lower pH limit and an upper pH limit and essentially insoluble at pH values lower than said lower pH limit or higher than said upper pH limit.

According to certain embodiments of the invention, the pH indicator is coated, at least partially, by two or more layers wherein at least two of these layers are having different pH-depending solubility properties.

The pH indicator of claim 1 wherein may be fabricated from any of plastic, wood, glass, metal, fabric or paper. According to a specific embodiment the substrate is a pH indicator strip impregnated with one or more pH indicator compounds.

The substances that constitute the coating layer may be any substance that is having pH-dependent solubility properties including amino acids, peptides, polypeptides, proteins, fatty acids, lipids, natural or synthetic polymers or a combination thereof.

The invention further relates to articles containing the novel pH indicator of the invention.

BRIEF DESCRIPTION OF THE DRAWINGS

The present invention will be understood and appreciated more fully from the following detailed description taken in conjunction with the drawings in which:

FIGS. 1A and 1B are a plan view and a transverse cross sectional view, respectfully, of a first embodiment of a pH indicator of the invention;

FIGS. 2a and 2b are a plan view and a transverse cross sectional view, respectfully, of a second embodiment of a pH indicator of the invention;

FIGS. 3a and 3b are a plan view and a transverse cross sectional view, respectfully, of a third embodiment of a pH indicator of the invention;

DETAILED DESCRIPTION OF THE PREFERRED EMBODIMENT

Figure 4:
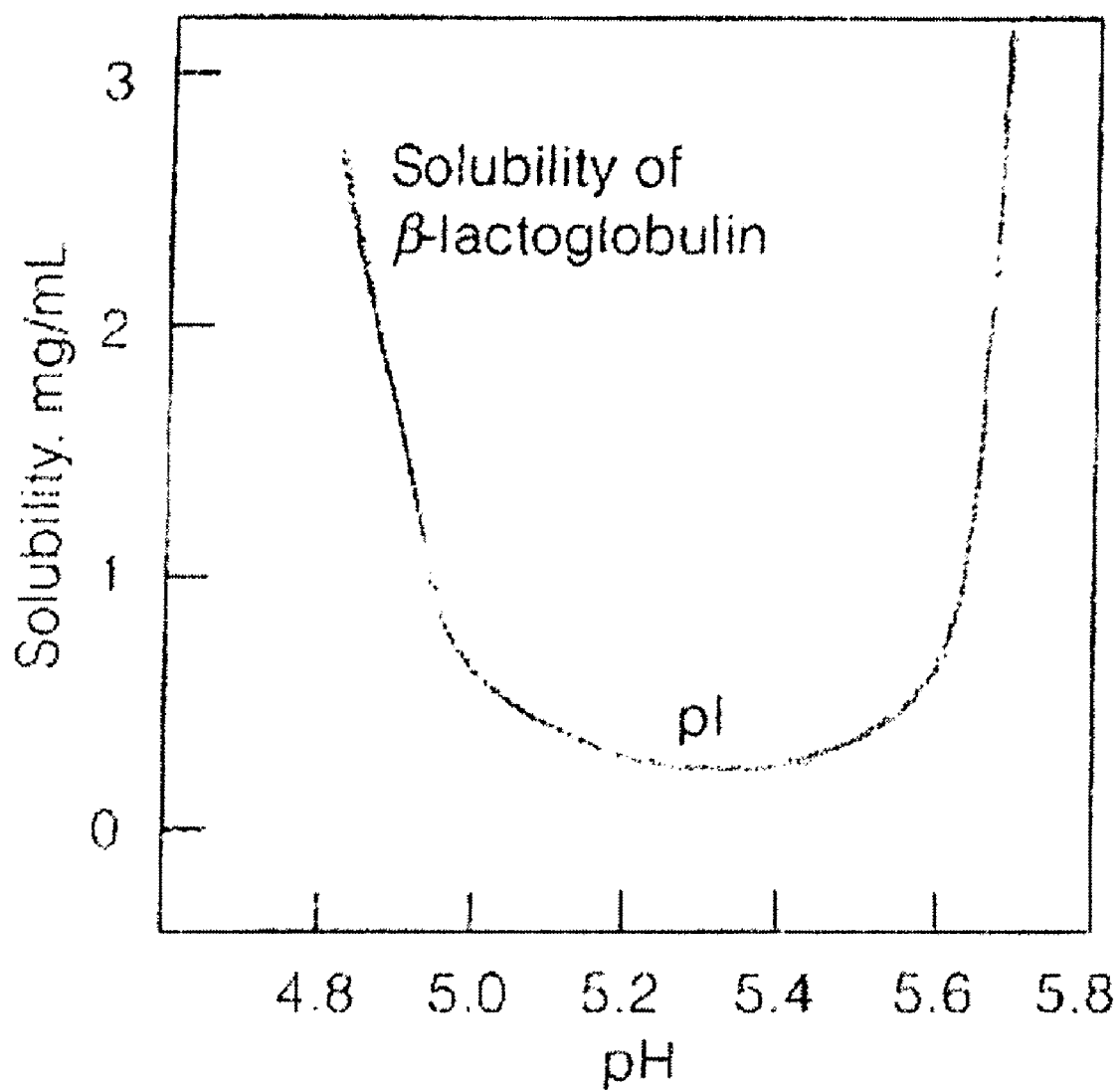
FIG. 4 is a solubility graph of β-lactoglobulin as function of pH, given as an example for pH depending solubility behavior.

The present invention provides a novel type of pH indicators which can be designed to provide a full spectrum of pH indicators for detecting predetermined pH transitions.

Generally, the pH indicators of the invention comprise a solid substrate coated by at least one layer of one or more substances, wherein the solid substrate and the coat are having different, easily distinguishable, colors. The substances that constitute the coat layer are having pH-depending solubility properties and are selected so as to dissolve when brought in contact with a liquid of a predetermined pH range, thereby exposing the substrate underneath. For all other pH value outside said predetermined pH range the coat remains unchanged. Thus, upon exposure, the color of the substrate provides a clear visible signal.

The solid substrate may be any inert solid that does not dissolve or react under any pH value for which the indicator is designed. Preferably, the substrate is selected depending upon the type of media of the application for which it is designed so as not to react with other materials that might be present in the media. Possible substrate materials include, but are not limited to, plastic (e.g., polypropylene, polyethylene, polyester, copolymers etc.), wood, glass, metal, fabric and paper. The solid substrate may be rigid or flexible for best fitting the application for which it is designed. The substrate may be colored by any known technique either by incorporating the color in the form of a pigment or dye, during the fabrication of the substrate or by painting or dying the substrate, providing the pigment or dye does not react or leach under pH changes. In accordance with a preferred embodiment of the invention, the substrate is fabricated from colored plastic sheets.

It will be realized that one of the advantages of the present invention is that the color of the substrate, namely the signal color, can be selected to be any color, thus allowing choosing a color which is having a large contrast with the color of the coat. This is in contrast with known pH indicator strips, where the color change is an inherent property of the indicator.

In accordance with the designated application for which the indicator is designed, either both faces, or only one face of the solid substrate may be coated. The coating may be applied in the form of a continuous layer to cover the whole face or in a discontinuous form to form a particular pattern on the substrate surface. FIGS. 1 through 3, illustrate different configurations of the pH indicator stick of the invention. It will be realized that although the general shape of the indictor as depicted in the figures is an elongated strip, the indicator may assume any other shape and form. Thus, the indicator may be shaped and dimensioned to best fit the application for which it is designated. FIG. 1 depict a first embodiment of a pH indicator of the invention, generally designated 10, according to which both surfaces of the solid substrate 15 are coated by a layer 18. Embodiment 10 fits applications where the indicator is immersed in a liquid and where both faces of the indicator are visible. For example indicator 10 may be used as an indicator for detecting spoilage of a food liquid product such as milk, sold in a container. A separate compartment, within or attached to the container and visible from the outside may contain a small volume of the liquid and an indicator of the invention, designed to expose the substrate when the pH drops below a predetermined value, is immersed inside the compartment. FIG. 2 depict another embodiment of a pH indicator, designated 20, according to which only one surface of substrate 25 is coated by a layer the 28. Embodiment 20 is suitable for applications where only one face of the indicator is visible. For example, indicator 20 may be incorporated into panty shields for detecting elevation of pH of vaginal fluids above 4.6. FIG. 3 depict yet another embodiment, designated 30, according to which the coated layer is applied to surface 31 of substrate 35 only partially in a discontinuous manner so as to form a particular pattern 38, a star in this specific example, that changes color when the coat layer dissolved. Pattern 38 may be in the form of alphanumeric characters, geometric shapes, symbols etc. In this embodiment, the area of the substrate underneath coat layer 38 is having a color which forms a contrast with the color of the coat layer while the rest of surface 31 may have the same color as the coat layer such that the pattern becomes visible only when the coat layer dissolved. The indicators of the invention, as illustrated in embodiments 10, 20 and 30, may be fabricated by first coating large sheets of substrate and then cut the sheets to the desired dimensions, thus reducing the manufacturing time required for coating each indicator individually. The substances that form a coating layer of a specific indicator are solid at the working temperature range for which the indicator is designed. Preferably, the coating substances are of a white or a light color that will not color the surrounding of the indicator upon dissolution.

The substances that form the coating layer are selected to have pH-depending solubility properties so that they essentially dissolve only under certain pH values but remain intact under other pH values. In accordance with different embodiments, the range at which the coat layer dissolve may have a lower limit, namely, the coat dissolves at pH>X; an upper limit, i.e., the coat dissolves at pH<Y; a limited range bound by a lower and an upper limit, i.e., the coat dissolves at X<pH<Y; or may be insoluble between a lower and an upper limit and soluble at pH<X and pH>Y where Y>X. The last embodiment is particularly useful in cases where X and Y correspond to the lower and an upper limits of the "normal" pH range of a test sample while any deviation above or below this range is an indication for an abnormal condition. Further, in accordance with a specific embodiment of the invention the substrate may be a conventional pH paper indicator strip, namely a strip impregnated with a pH indicator compound. The selection of a conventional pH indicator strip as the substrate of the pH indicator of the invention is particularly useful when the indicator is designed for indicating both elevation beyond or drop below normal pH range. By appropriate selection of the conventional pH indicator strip as the substrate, the color of the exposed pH paper will indicate whether the deviation is below or above the normal rage.

In accordance with other embodiments of the invention, more than one coating layer can be used wherein each of the layers is having different pH-depending solubility properties and wherein the combination of the layers exposes the substrate (i.e., gives a visible signal) at the desired pH transition. Such combination embodiments may be required when it is not possible to obtain the desirable solubility profile by only one layer. For example, consider a case where a test sample is having an initial pH value of 10 and an indicator is to be designed which will give a signal when and if the pH drops down to 5 but there is no one compound that is hydrophobic (i.e., is insoluble) at 5<pH<10 and hydrophilic (i.e., soluble) at pH<5. In this case a combination of three layers: an outermost layer insoluble in the range 7<pH<10; an intermediate layer insoluble between 6<pH<9; and an inner layer insoluble between 5<pH<6.5, will provide the desired behavior since the first (outermost) layer will dissolve when the pH drops to 7, the second (intermediate) layer will dissolve when the pH further drops to 6 and the inner layer will dissolve when the pH reaches 5, thereby exposing the substrate. It will be realized that the above example is given for illustrative sake only and should not be interpreted by any way as a concrete example. Another case where the combination embodiment is particularly useful is when a test sample undergoes a non-monotonic pH change, such that the pH may pass through the same pH value more than once but it is only the second time that the solution reaches this value that is to be indicated. In such a case a combination of layers may be designed such as to provide the desirable behavior by incorporating an intermediate layer that will remain intact the first time the sample reaches this specific value but which will dissolve later under different pH values to expose the final innermost layer which is selected to dissolve when the sample reaches this specific pH value again, thereby exposing the substrate.

It will be realized that the terms "soluble" and "insoluble" when used to describe the coating layer of the present pH indicator are used in relation to the particular application (namely the test sample) for which the indicator is designed. Thus, the amount of the coating substance (i.e., area and layer thickness) could be selected in accordance with the conditions and volume of the expected test sample and the specific use of the indicator. The appropriate amount for a specific application can be determined for example by calibration with test samples.

The substances that form the coating layer may be selected from any compounds known to have pH-depending solubility properties or may be tailored specifically for the purpose of the present invention by modifying known compounds. Such compounds may include for example polymeric compounds used for controlled release of active ingredients through pH control such as used in pharmaceutical applications for pH-controlled release of drugs or in the cleaning industry for pH-controlled release of detergent and wash additives. Such polymeric compounds may be tailored to exhibit a specific pH-dependent solubility characteristics by manipulating the ratios between ionic groups and hydrophobic groups in side-chains.

In particular suitable for the present invention are compounds which are having more than one ionized form including amino acids, peptides, polypeptides and proteins, and/or are having a hydrophobic moiety and a hydrophilic moiety including amphipathic substances such as fatty acids and lipids. Certain amino acids and peptides as well as proteins which carry both positive and negative ionic groups at their side chains are particularly suitable as tend to be soluble when they have a net charge, i.e., at pH values above or below their isoelectric point but have a minimum solubility at their isoelectric point. FIG. 4 is an example of the pH-depending solubility behavior of β-lactoglobulin (from "Biochemistry", C. K. Mathews, K. E. van Holde and K. G. Ahren, Addison Welsley Longman, Inc., third addition, p. 48).

The coating compounds can be applied to the substrate from the melt or from solution in any conventional manner including dipping the substrate in the melt or the solution, spraying the melt or solution on the substrate, brushing the melt or solution onto the substrate, or pouring the melt or solution over the substrate. When applied from solution the solvent is subsequently removed to leave the substance on the substrate. When appropriate an intermediate binder may be used to adhere the substance onto the substrate. In accordance with other embodiments, the substance may be molded to form hollow molds into which the substrate may be inserted and sealed.

The indicator sticks of the invention can be used as stand-alone sticks to be dipped into a test sample or may be incorporated into a variety of articles such as food containers, panty shields, hygienic napkins, diapers and more.

It will be appreciated by persons skilled in the art that the present invention is not limited to what has been particularly shown and described hereinabove. Rather the scope of the present invention is defined only by the claims which follow.

The invention claimed is:

1. A pH indicator for detecting a predetermined pH change in a liquid, the pH indicator comprising a solid substrate coated at least partially by at least one layer of at least one substance having pH-dependent solubility, wherein said at least one layer is having a first color and said substrate is having a second color different from the first color and wherein said at least one substance is selected to dissolve or to decompose only when exposed to a liquid having a pH value in a predetermined pH range, thereby when the layer is dissolved or decomposed said substrate and second color are exposed which indicated the predetermined pH range has been reached.

2. The pH indicator of claim 1 wherein said at least one layer is essentially insoluble at pH values lower than a predetermined pH value and essentially soluble at pH values higher than said preselected pH value.

3. The pH indicator of claim 1 wherein said at least one layer is essentially insoluble at pH values higher than a predetermined pH value and essentially soluble at pH values lower than said preselected pH value.

4. The pH indicator of claim 1 wherein said at least one layer is essentially insoluble in a pH range delimited by a lower pH limit and an upper pH limit and essentially soluble at pH values lower than said lower pH limit or higher than said upper pH limit.

5. The pH indicator of claim 1 wherein said at least one layer is essentially soluble in a pH range delimited by a lower pH limit and an upper pH limit and essentially insoluble at pH values lower than said lower pH limit or higher than said upper pH limit.

6. The pH indicator of claim 1 wherein said substrate is fabricated from any one of the following: plastic, wood, glass, metal, fabric or paper.

7. The indicator of claim 1 wherein said at least one substance is selected from the group consisting of amino acids, peptides, polypeptides, proteins, fatty acids, lipids and a combination thereof.

8. The indicator of claim 1 wherein said at least one substance is a polymer having a pH-depending solubility properties.

9. The indicator of claim 1 wherein said at least one layer comprises two or more layers and wherein at least two of said two or more layers are having different pH-depending solubility properties.

10. The indicator of claim 1 wherein the substrate is having a first face and a second opposite face and wherein both faces are at least partially coated by said at least one layer.

11. The indicator of claim 1 wherein the substrate is having a first face and a second opposite face and wherein only one of said first and second faces is at least partially coated by said at least one layer.

12. The indicator of claim 1 wherein said at least one layer is applied to at least one face of the substrate in a discontinuous manner to form a predetermined pattern.

13. An article containing the pH indicator of claim 1, said article is selected from the group consisting of food products and disposable absorbent articles.

14. The article according to claim 13, wherein said disposable absorbent article is selected from the group consisting of a hygienic pad and a panty shield.

* * * * *